(12) United States Patent
Barrau et al.

(10) Patent No.: US 11,774,784 B2
(45) Date of Patent: Oct. 3, 2023

(54) OPTICAL SYSTEM FOR TREATING CHRONOBIOLOGICAL DISORDERS AND/OR MYOPIA

(71) Applicant: ESSILOR INTERNATIONAL, Charenton-le-Pont (FR)

(72) Inventors: Coralie Barrau, Charenton-le-Pont (FR); Denis Cohen Tannoudji, Charenton-le-Pont (FR); Thierry Villette, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 249 days.

(21) Appl. No.: 17/248,704

(22) Filed: Feb. 3, 2021

(65) Prior Publication Data

US 2021/0157172 A1 May 27, 2021

Related U.S. Application Data

(63) Continuation of application No. 16/092,662, filed as application No. PCT/EP2017/058554 on Apr. 10, 2017, now Pat. No. 10,942,373.

(30) Foreign Application Priority Data

Apr. 11, 2016 (EP) ..................... 16305422

(51) Int. Cl.
*G02C 7/10* (2006.01)
*A61N 5/06* (2006.01)
(Continued)

(52) U.S. Cl.
CPC .............. *G02C 7/104* (2013.01); *A61F 9/022* (2013.01); *A61N 5/0618* (2013.01); *G02B 5/20* (2013.01);
(Continued)

(58) Field of Classification Search
CPC .... G02C 7/104; G02C 7/107; G02C 2202/24; A61F 9/022; A61N 5/0618; A61N 2005/0626; A61N 2005/063; A61N 2005/0648; A61N 2005/0651; A61N 2005/0662; A61N 2005/0663;
(Continued)

(56) References Cited

U.S. PATENT DOCUMENTS 6,235,046 B1  5/2001  Gerdt
8,062,444 B2  11/2011 Begon et al.
(Continued)

FOREIGN PATENT DOCUMENTS

BE  1018173  6/2010
EP  2026950  1/2011
(Continued)

*Primary Examiner* — Tuyen Tra
(74) *Attorney, Agent, or Firm* — Norton Rose Fulbright US LLP

(57) ABSTRACT

An optical system having a spectral transmission profile having an average transmittance Ta between 380 nm and 780 nm and an average red light transmittance Tr between a first limit L1 and a second limit L2, with Tr<2*Ta/3 and L1=600 nm and L2=780 nm, and the optical system being configured to allow selectively retinal exposure of an eye to at least one selected range of wavelengths of light in the visible spectrum of 460 nm to 530 nm.

13 Claims, 2 Drawing Sheets

(51) Int. Cl.
  *G02B 27/01* (2006.01)
  *A61F 9/02* (2006.01)
  *G02B 5/20* (2006.01)
  *G02B 5/28* (2006.01)
(52) U.S. Cl.
  CPC .......... *G02B 5/28* (2013.01); *G02B 27/0172* (2013.01); *G02C 7/107* (2013.01); *A61N 2005/063* (2013.01); *A61N 2005/0626* (2013.01); *A61N 2005/0648* (2013.01); *A61N 2005/0651* (2013.01); *A61N 2005/0662* (2013.01); *A61N 2005/0663* (2013.01); *A61N 2005/0667* (2013.01); *G02B 2027/0174* (2013.01); *G02B 2027/0178* (2013.01); *G02C 2202/24* (2013.01)
(58) Field of Classification Search
  CPC .... A61N 2005/0667; G02B 5/20; G02B 5/28; G02B 27/0172; G02B 2027/0174; G02B 2027/0178

USPC ...................... 351/41, 159.01, 159.6, 159.65
See application file for complete search history.

(56) References Cited

U.S. PATENT DOCUMENTS

| | | | |
|---|---|---|---|
| 8,534,853 | B2 | 9/2013 | Ligas et al. |
| 10,942,373 | B2 * | 3/2021 | Barrau ................... G02C 7/104 |
| 2013/0278887 | A1 | 10/2013 | Legerton |

FOREIGN PATENT DOCUMENTS

| | | |
|---|---|---|
| EP | 2772794 | 9/2014 |
| WO | WO2007/088312 | 8/2007 |
| WO | WO2010/109154 | 9/2010 |
| WO | WO2012/044256 | 4/2012 |
| WO | WO2012/106542 | 8/2012 |
| WO | WO2012/153072 | 11/2012 |
| WO | WO2013/004954 | 1/2013 |

* cited by examiner

OPTICAL SYSTEM FOR TREATING CHRONOBIOLOGICAL DISORDERS AND/OR MYOPIA

CROSS-REFERENCE TO RELATED APPLICATIONS

This application is a continuation of U.S. Ser. No. 16/092,662, filed Oct. 10, 2018, which is a national phase application under 35 U.S.C. § 371 of International Application No. PCT/EP2017/058554 filed 10 Apr. 2017, which claims priority to European Application No. 16305422.4 filed 11 Apr. 2016. The entire contents of each of the above-referenced disclosures is specifically incorporated by reference herein without disclaimer.

FIELD OF THE INVENTION

The invention relates to an optical system having a spectral transmission profile adapted for hormonal regulation and myopia control.

BACKGROUND OF THE INVENTION

Myopia is a very common vision condition affecting billions of people all over the world. Myopia causes visual inconvenience but can also have severe long term consequences on the eye that may even result in blindness. It appears that for most individuals, in particular for children, the myopia condition of the eye tends to increase with time.

Recent studies have evidenced that both genetic and environmental factors contribute to myopia development.

It is therefore crucial to slow or stop the progression of myopia, as the severity of its consequences is linked to the severity of the final myopia that is reached by the patient.

Recent studies point out natural light can help slow down myopia progression. In particular, it has been observed that outdoors activities slow down myopia progression.

Indeed, light is the most potent stimulus for entraining endogenous rhythms to the daily light cycle: sleep-wake cycle, mood, cognition, alertness, but also hormonal regulation, for instance dopamine production cycle . . . . Dopamine seems to be implied in the progression of the eye length, and thus implied in myopia progression. Low concentrations of retinal dopamine were shown to be associated with form deprivation myopia. Refractive development is associated with illuminance dependent dopamine release.

However, when individual and in particular children spend time outdoors, their eyes are also exposed to harmful light (UV, blue light). Solar lenses protect the eyes from the harmful effects of natural light but also appear to decrease the benefits of the outdoor activities on the myopia progression.

Therefore, there is a need for an optical system that provides protection for the eye from the harmful wavelength of natural light and maintains or even enhances the benefit of light stimulation on myopia progression and hormonal regulation.

One object of the present invention is to provide such optical system.

SUMMARY OF THE INVENTION

To this end, the invention proposes an optical system having a spectral transmission profile having an average transmittance Ta between 380 nm and 780 nm and an average red light transmittance Tr between a first limit L1 and a second limit L2, with $Tr<2*Ta/3$ and $L1=600$ nm and $L2=780$ nm, and the optical system being configured to allow retinal exposure of an eye to at least one selected range of wavelengths of light in the visible spectrum of 460 nm to 530 nm.

Advantageously, the optical system of the invention combines two optical approaches for light management: a red filtering and a blue-green light exposure (by emission/transmission). The optical system of the invention can be used to minimize or prevent from progressive myopia while optimizing light-induces hormonal regulation.

Indeed, the optical system according to the invention combines both actions of:

light exposure (emission/transmission) in a selected range of wavelengths for hormonal regulation, in particular regulation of dopamine which is implied in eye length, and selective light filtering over another specific range of wavelengths to deal with the chromatic effect suspected in myopia.

According to further embodiments which can be considered alone or in combination:

the optical system is configured to selectively emit light in at least one selected range of wavelengths of light in the visible spectrum of 460 nm to 530 nm $L2=650$ nm; and/or $Tr<Ta/5$; and/or $L2=700$ nm and $Tr<Ta/2$; and/or the spectral transmission profile has an average blue light transmittance Tb between a third limit L3 and a fourth limit L4, with $Tb<2Ta/3$, for example $Tb<Ta/5$, with $L3=380$ nm and $L4=455$ nm; and/or Tr is substantially equal to Tb; and/or The optical system is configured to solar protection;

the average transmittance Ta between 380 nm and 780 nm is greater than or equal to 50%; and/or the at least one selected range of wavelengths of light is centered on a wavelength within the range of 480 nm to 510 nm, with a bandwidth in a range from 20 nm to 70 nm; and/or the optical system further comprises at least a luminescent agent which emits light within the at least one selected range of wavelengths of light; and/or the optical system is configured to selectively emit light within the at least one selected range of wavelengths of light with an emission rate greater than or equal to 30% and preferably, greater than 95% and more preferably equal to 100%; and/or the luminescence agent is a phosphorescent material or a fluorescent material which emits light respectively by phosphorescence and by fluorescence in the at least one selected range of wavelengths of light; and/or the fluorescent material is a fluorescent molecule which absorbs energy between 380 nm and 455 nm of the light spectrum and re-emits it in the selected range of wavelengths of light; and/or the fluorescent material is a fluorescent molecule which absorbs energy in the UV portion of the light spectrum and re-emits it in the selected range of wavelengths of light; and/or the fluorescent material comprises fluorescents nanoparticules such as quantum dots; and/or the optical system is configured to selectively and substantially reflect light arriving on the front face of the optical system between L1 and L2 and/or L3 and L4; and/or the optical system comprises an interferential filter; and/or the optical system is a photonic crystal optical filter; and/or the optical system further comprises:

a light emitting source, an optical waveguide adapted to collect light emitted from the light emitting source and to guide the collected light to the eye of a wearer when the optical system is being worn by the wearer, a controller device adapted to control the emitted spectrum and/or radiance and/or light level emitted by the light emitting source so as to selectively emit light in the selected range of wavelengths; and/or the optical system further comprises an optical sensor adapted to detect the light level and/or spectrum of the ambient light, and wherein the controller device is configured so as to control the light emitting source based at least on the detected light level and/or radiance and/or spectrum of the ambient light; and/or the controller device is configured so as to control the light emitting source based on at least one of:

the day time, the geo-localization of the optical system, wearer data relating to the age of the wearer and/or the biological clock of the wearer and/or the activity of the wearer and/or ocular disease of the wearer and/or the type of physiological disorder of the wearer; and/or the controller device is configured so as to provide gradient irradiances; and/or the controller device is configured so as to provide spatially modulated irradiances; and/or the optical system further comprises an eye tracking device adapted to detect position and/or movement of the eye of the wearer, and wherein the controller device is configured so as to control the light emitting source based at least on the detected position and/or movement of the eye of the wearer; and/or the optical waveguide comprises refractive optics, for example mirrors, prism combiner, semi-reflective diopter, Light guide optical element; and/or the optical waveguide comprises diffractive optics, for example embedded grating and/or holographic optical elements; and/or the optical waveguide comprises Fourier optics; and/or the optical waveguide comprises multiplexed beam splitters; and/or the light emitting source comprises one or several colored LEDs, for example blue-green LEDs; and/or the controller device is configured so as to provide chronobiology regulation or synchronisation and/or affective disorders regulation and/or myopia prevention and/or reduction and/or epilepsy palliative treatment by controlling the light emitting source to provide emission between 460 nm and 530 nm with specific spatial and temporal patterns; and/or the optical system further comprises an optical lens mounted in a spectacle frame.

The invention, further relates to using the optical system according to the invention in treating chronobiological disorders and/or myopia.

As used herein, the term optical lenses includes optical lenses such as ophthalmic lenses and semifinished lens. Ophthalmic lenses are meant a lens adapted to a spectacle frame to protect the eye and/or correct the sight. Ophthalmic lenses may be corrective and non-corrective lenses and also visors, shields, masks, goggles and other vision devices intended to be worn in front of the eyes. As used herein, an optical substrate is understood to mean an uncoated substrate, generally with two main faces corresponding in the finished ophthalmic lens to the front and rear faces thereof. The bulk is particularly made of an optical transparent material, generally chosen from transparent materials of ophthalmic grade used in the ophthalmic industry, and formed to the shape of an optical device.

The optically transparent material may be a mineral or organic glass. Examples of organic glasses are those made of thermoplastic or thermosetting resin. If the transparent material is an organic glass made of thermoplastic, the thermoplastic may be selected from the group consisting of polyamides, polyimides, polysulfones, polycarbonates, polyethylene terephthalate, poly(methyl(meth)acrylate), cellulose triacetate, and copolymers thereof. If the transparent material is an organic glass made of thermosetting resin, the thermosetting resin may be selected from the group consisting of cycloolefin copolymers, homopolymers and copolymers of allyl carbonates of linear or branched aliphatic or aromatic polyols, homopolymers and copolymers of (meth) acrylic acid and esters thereof, homopolymers and copolymers of thio(meth)acrylic acid and esters thereof, homopolymers and copolymers of allyl esters, homopolymers and copolymers of urethane and thiourethane, homopolymers and copolymers of epoxy, homopolymers and copolymers of sulphide, homopolymers and copolymers of disulphide, homopolymers and copolymers of episulfide, and combinations thereof.

As used herein, the term coating is understood to mean any layer, layer stack or film which may be in contact with the optical substrate and/or with another coating, for example a sol-gel coating or a coating made of an organic resin. A coating may be deposited or formed through various methods, including wet processing, gaseous processing, and film transfer. The functional coatings classically used in optics may be, without limitation, an impact-resistant and/or adhesion primer, an abrasion-resistant and/or scratch-resistant coating, an anti-reflection coating, an antistatic coating, an anti-soiling coating, an anti-reflective coating, an anti-smudge coating, an anti-dust coating, an anti-fog coating, a water repellent coating, an anti-scratch coating, an interferential filter, a tinted coating, a mirror coating, a photochromic coating, and a combination of any of preceding compatible coatings, especially an impact-resistant primer coating coated with an abrasion and/or scratch-resistant coating.

Abrasion- and/or scratch-resistant coatings (hard coatings) are preferably hard coatings based on poly (meth) acrylates or silanes. Recommended hard abrasion- and/or scratch-resistant coatings in the present invention include coatings obtained from silane hydrolyzate-based compositions (sol-gel process), in particular epoxysilane hydrolyzate-based composition.

The primer coatings improving the impact resistance and/or the adhesion of the further layers in the end product are preferably polyurethane or acrylic. Primer coatings and abrasion-resistant and/or scratch-resistant coatings may be selected from those described in the application WO 2007/088312 or WO2013/004954.

The antireflection coating, which improves the antireflecting properties of the final optical article by reducing the light reflection at the article-air interface over a relatively large range of the visible spectrum, may be any antireflection coating classically used in the optics field, in particular in ophthalmic field. As is well known, antireflective coatings traditionally comprise a monolayered or a multilayered stack composed of dielectric or sol-gel materials or hybrids materials (hybrid material means that said multilayered stack may comprise at least a layer comprising carbon atom, oxygen atom, and at least a metal or metalloid which is selected from silicium, zirconium, titane and niobium). These are preferably multilayered coatings, comprising layers with a high refractive index (HI, n>1.5) and layers with a low refractive index (LI, n≤1.5).

The structure and preparation of antireflection coatings are described in more details in patent application WO 2010/109154 and WO 2012/153072.

The antireflection coating may present specific reflection spectra. More particularly, in an embodiment of the invention, the optical article may comprise an antireflective coating which present a low reflection both in the ultraviolet region and in the visible region, as described in U.S. Pat. No. 8,534,853.

Coatings such as primers, hard coats and antireflection coatings according to the invention may be deposited using methods known in the art, including spin-coating, dip-coating, spray-coating, evaporation, sputtering, chemical vapor deposition and lamination. By lamination it is understood, that a flat thermoplastic film comprising at least one of said coating intrinsically or on its surface is glued to an optical substrate, directly on it or on a previous coating deposited on said optical substrate. The lamination may be done and the front and/or the rear face of the optical substrate as described in the following patents EP2026950 and U.S. Pat. No. 8,062,444.

As used herein, a coating that is "on" a substrate/coating or which has been deposited "onto" a substrate/coating is defined as a coating that (i) is positioned above the substrate/coating, (ii) is not necessarily in contact with the substrate/coating, that is to say one or more intermediate coating(s) may be interleaved between the substrate/coating and the relevant coating (however, it does preferably contact said substrate/coating), and (iii) does not necessarily completely cover the substrate/coating. When "a layer 1 is arranged under a layer 2", it is intended to mean that layer 2 is more distant from the substrate than layer 1.

BRIEF DESCRIPTION OF THE DRAWINGS

Embodiments of the invention will now be described, by way of example only, and with reference to the following drawings in which.

Figure 4:
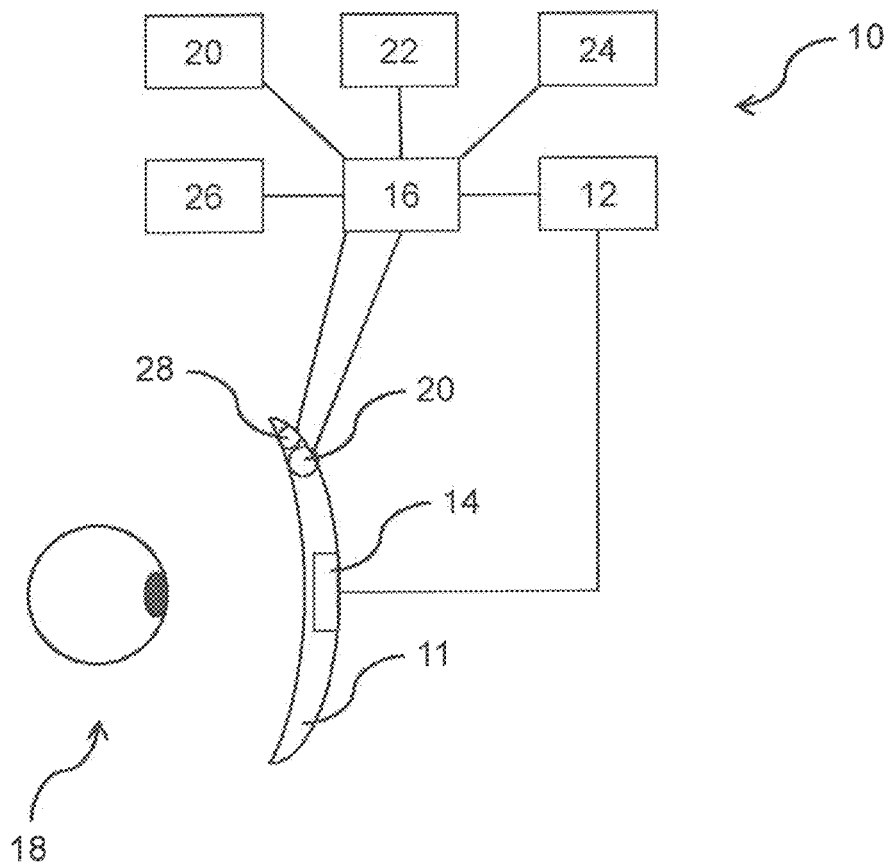
FIG. 4 is a schematic block diagram representing an eye of a wearer and an optical system according to an embodiment of the invention.

Elements in FIG. 4 are illustrated for simplicity and clarity and have not necessarily been drawn to scale. For example, the dimensions of some of the elements in the figure may be exaggerated relative to other elements to help improve the understanding of the embodiments of the present invention.

DETAILED DESCRIPTION OF PREFERRED EMBODIMENTS

The invention relates to optical system having a selectively filtering effect over a specific range of wavelengths and configured to selectively allow retinal exposure of an eye to at least one selected range of wavelengths of light. The optical system according to the invention may be a head mounted system, for example a spectacle frame comprising optical lenses, such as ophthalmic lenses.

Each optical lens comprises an optical substrate having a first surface and a second surface.

In the specific embodiment of an optical lens, the first surface is a concave back/posterior surface, disposed proximal to an eye of a wearer in use and the second surface is a convex front/anterior surface disposed in use distal to the eye.

The optical system according to the invention has a spectral transmission profile having an average transmittance Ta between 380 nm and 780 nm and an average red light transmittance Tr between between a first limit L1 and a second limit L2 with Tr<2*Ta/3 and L1=600 nm and L2=780 nm.

According to an embodiment of the invention, L2 may be equal to 700 nm and Tr<Ta/2.

According to an embodiment of the invention, L2 may be equal to 650 nm and Tr<Ta/5.

In the sense of the invention the "average transmittance" over a given range of wavelengths $(\lambda 1, \lambda 2)$ corresponds to $\int_{\lambda 1}^{\lambda 2} T(\lambda) d\lambda$, with $T(\lambda)$ the transmittance of the optical system as a function of the wavelength. The transmittance corresponds to the fraction of incident light that is transmitted through the optical system.

The average transmission Ta of the optical system between 380 nm and 780 nm is greater than or equal to 50%.

According to an embodiment of the invention, the optical system is configured to have an average transmittance Ta between 380 nm and 780 nm from 3% to 43% (i.e. at an inhibition rate of 97% to 57%) for example depending on the level of solar protection required such as class 0 to 4 as defined by International standards such as NF EN 1836+ A1_2007E or ISO_DIS 12312-1 E.

More precisely, the average transmittance Ta could be:
greater than or equal to 18% and smaller than or equal to 43%, so as to provide an optical system adapted for average luminosity environments, or
greater than or equal to 8% and smaller than or equal to 17%, so as to provide an optical system adapted for high luminosity environments, or
greater than or equal to 3% and smaller than or equal to 8%, so as to provide an optical system adapted for very high luminosity environments.

In another embodiment, the optical system is configured to have an average transmittance in the visible spectrum comprised between 80% and 100% (i.e. at an inhibition rate of 20% to 0%).

Additionally, the optical system of the invention may be used in protecting at least part of an eye of a user from harmful ultraviolet light and/or harmful blue light.

Indeed, the optical system may have a spectral transmission profile having an average blue light transmittance Tb between a third limit L3 and a fourth limit L4, with Tb<2Ta/3, for example Tb<Ta/5, with L3=380 nm and L4=455 nm.

According to an embodiment of the invention the average red light transmission Tr over L1 and L2 is substantially equal to the average blue light transmission Tb over between L3 and L4.

In an embodiment, the spectral transmission profile of the optical system may be achieved by an optical filter.

The optical filter may be obtained through an absorptive filter, an interferential filter or a combination thereof, in order to define the desired spectral transmittance profile.

The interference filters may be coated on the front face and/or the rear face of the optical substrate such as any functional coating or can be applied onto a functional coating.

With respect to absorptive filters, they may comprise as example and without any limitation, dye, pigment, absorber and combination thereof known in the art.

The absorptive filter can be applied onto a functional coating of the optical lens, by coating a solution or film lamination thanks to various methods, amongst which are wet processing, gaseous processing, film transfer and lamination process, such as spin-coating, dip-coating, spray-coating, vacuum deposition, evaporation, sputtering, chemical vapour deposition.

Alternatively or additionally, the absorptive filter comprises at least a dye and/or pigment, dispersed within a thermoplastic or thermosetting polymer. The dye and/or pigment may be added to the monomers of the polymer before cross-linking process and then imprisoned within the polymer during cross-linking process.

In one particular example, the thermoplastic or thermosetting polymer comprising the dye and/or pigment is an additional layer applied on the optical lens.

In another particular example, the optical substrate of the optical lens includes at least one dye and/or pigment.

Depending on the spectral transmission profile, the interferential filter as described above may be configured accordingly, or the appropriate choice of absorptive material described above may be made.

The red light transmission rate may be adjusted by increasing the number of absorptive or interferential layers of the optical filter.

According to an embodiment of the invention the optical system is configured to selectively and substantially reflect light arriving on the front face of the optical system, i.e. the incident light, with wavelengths comprised between L1 and L2 and/or L3 and L4.

So as to selectively and substantially reflect light, the optical system according to the invention may comprise an interferential filter.

In an exemplary embodiment, the interferential filter is an interferential coating.

The interferential filter may be manufactured using interferential technologies such as dielectric multi-layers with variable optical refractive indexes, photonic band gap materials such as liquid cristal technology, cholesteric crystals or MOF technology, or holographic gratings and any combination thereof.

In exemplary embodiments, the interferential filter may be coated on the front face of the optical system such as any functional coating, e.g. anti-reflection coating, mirror coating or can be applied onto a functional coating thanks to various methods as those disclosed for the incorporation of luminescent agents described in greater details further in the description and known form the state of art.

In one exemplary embodiment of the invention, the interferential coating of the front face of the optical system may comprise a stack of layers of dielectric materials with a combination of layers of high refractive index (HI, n>1.5), and layers of low refractive index (LI n≤1.5) configured to define the spectral reflectance profile according to the invention.

In one embodiment, the optical filter may be obtained through a photonic crystal optical filter in order to define the desired spectral transmission profile according to the invention.

The photonic crystal optical filter may be manufactured using photonic band gap materials.

The optical system according to the invention is further configured to selectively allow retinal exposure of an eye to at least one selected range of wavelengths of light in the visible spectrum of 460 nm to 530 nm, preferably of 480 nm to 520 nm (herewith defined as the selected range of wavelengths of light or chronobiological blue light)

In an embodiment, the retinal exposure of a wearer respective eye may be achieved by an optical filter configured to allow selectively substantial transmission of the selected range of wavelengths of light.

The optical filter may be obtained through an absorptive filter, an interferential filter or a combination thereof, in order to define the desired light transmittance profile.

The interference filters may be coated on the front face and/or the rear face of the optical substrate such as any functional coating or can be applied onto a functional coating.

With respect to selective absorptive filters, they may comprise as example and without any limitation, dye, pigment, absorber and combination thereof known in the art.

The absorptive filter can be applied onto a functional coating of the optical lens, by coating a solution or film lamination thanks to various methods, amongst which are wet processing, gaseous processing, film transfer and lamination process, such as spin-coating, dip-coating, spray-coating, vacuum deposition, evaporation, sputtering, chemical vapour deposition.

Alternatively or additionally, the absorptive filter comprises at least a dye and/or pigment, dispersed within a thermoplastic or thermosetting polymer. The dye and/or pigment may be added to the monomers of the polymer before cross-linking process and then imprisoned within the polymer during cross-linking process.

In one particular example, the thermoplastic or thermosetting polymer comprising the dye and/or pigment is an additional layer applied on the optical lens.

In another particular example, the optical substrate of the optical lens includes at least one dye and/or pigment.

Depending on the selected range wavelength of transmission, the selective interferential filter as described above may be configured accordingly, or the appropriate choice of absorptive material described above may be made.

The transmission rate of the optical filter in the selected range wavelength of transmission may be configured according to the use envisaged and/or the level of protection required.

The transmission rate may be adjusted by increasing the number of absorptive or interferential layers of the optical filter.

In other embodiments, the optical system is configured to selectively emit light in at least the selected range of wavelengths of light in the visible spectrum.

Advantageously, combining light therapy with red light filtering may be used to minimize or prevent from progressive myopia.

In preferred embodiments, the selected range of wavelengths of light is centered on a wavelength within the range 480 nm to 510 nm with a bandwidth from 20 nm to 70 nm.

In a first preferred exemplary embodiment, the range of wavelengths is centered on a wavelength of substantially 480 nm with a bandwidth from 20 nm to 40 nm.

In a second preferred exemplary embodiment, the range of wavelengths is centered on a wavelength of substantially 490 nm with a bandwidth from 20 nm to 40 nm.

The optical system of the invention may be configured to emit light within the at least one selected range of wavelengths with an emission rate greater than or equal to 30%, for example within the range 50% to 100%, and preferably, greater than 95% and more preferably equal to 100%.

Indeed, an optical system according to the invention provides an increase of the retinal exposure within the blue-green light range of the visible spectrum, i.e. the chronobiological blue light.

As already mentioned, such chronobiological blue light is the best synchronizer of human non visual biological functions.

By optimizing retinal light reception in between 460 nm and 500 nm, we induce the direct stimulation of ipRGCs by melanopsin photoreception peaking at 480 nm for humans.

In particular, this specific illumination range is the most potent stimulus for entraining endogenous rhythms to the daily light cycle with the two photoreceptive processes involved: the melanopsin-driven phototransduction mechanism within the ipRGC itself, peaking near 480 nm and indirect photoreception in rods, peaking near 500 nm.

Therefore, optical systems according to embodiments of the invention may be used in therapy and/or disease prevention.

In particular, they may be used in therapy for treatment of subjects suffering from chronobiological disorders such as circadian rhythm sleep disorders (jet lag delayed and advanced sleep phase syndroms), hormonal troubles, cognition and memory disorders, psychomotor disorders, body temperature deregulation, mood disorders, alertness disorders, neurobehavioral troubles, seasonal affective disorders such as fatigue and depression.

Indeed, the optical system according to the invention can compensate inadequate lighting conditions (lack of beneficial blue) to help the biological clock to remain synchronized through the good blue/melatonin secretion relationship.

The optical system to any embodiment of the invention may be configured to enhance the constriction of the pupil of the eye, providing enhanced protection of the eye against harmful wavelengths, i.e. red light, UV and/or blue-violet harmful light.

Furthermore, advantageously, an optical system according to any embodiment of the invention may be used to improve visual acuity of the wearer.

The decrease in pupil size should reduce to some extent the deleterious effects on visual acuity of the optical aberrations and stray light.

According to an embodiment of the invention, the optical system comprises at least a luminescent agent which emits light in the at least one selected range of wavelengths of light.

The luminescence agent may be a phosphorescent material or a fluorescent material which emits light, respectively, by phosphorescence and by fluorescence in the selected range of wavelengths of light.

As well known, a fluorescent material absorbs light energy of a specific wavelength and re-emits light at a longer, but also visible, wavelength without reflecting substantial amounts of radiation.

The chemical nature of the fluorescent material is not particularly limited, provided that it is capable of emitting light by fluorescence, ideally a maximum emission peak, at a wavelength ranging from 460 to 510 nm, preferably from 480 to 500 nm.

Advantageously, the fluorescent material does not present any angular sensitivity.

In a non-limitative way, the fluorescent material may be an organic fluorophore dye or fluorescents nanoparticules such as quantum dots.

The fluorescent materials may be used singly or in combination.

The fluophore may be chosen, without limitation to these families, from Xanthen, Acridine, Oxazine, Polyene, Cyanine, Coumarin, combined heteroaromatics such as thiazoles, oxadiazoles such as Benzimidazolen, Tetrapyrole such as Porphin, Oxonol, Indolenine, Azamethine, Styril, Anthraquinone, Naphtalimide, Aza[18]annulene, Metal-ligand complexes, Squaraine, 8-hydroxyquinolone derivative, Polymethine, Perylene, Phtalocyanine, Diketopyrrolopyrole and any derivative or combination thereof.

In a first exemplary embodiment, the fluorescent material may be a fluorescent molecule that absorbs light in the UV and/or violet region of light (usually defined with the range 340 nm to 400 nm) and re-emits light by fluorescence mainly in the selected range of wavelengths of light.

Figure 1:
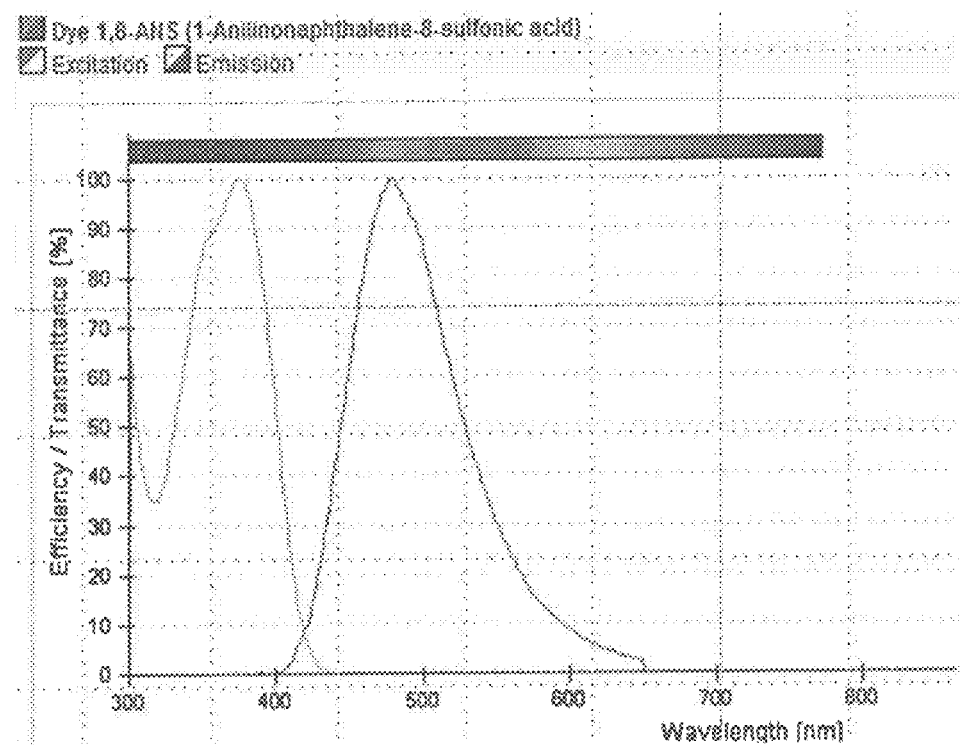
FIGS. 1 to 3 illustrate the emission and excitation spectrums of different fluophores used in an optical system according to an embodiment of the invention.

In a non-limitative example illustrated in FIG. 1, the fluorescent molecule used may be 1-anilinonaphtalene-8-sulphonic acid which has a maximum wavelength of absorption of 375 nm and a maximum wavelength of emission of 480 nm.

Advantageously, the fluorescent material allows substantial blocking of the harmful UV light while allowing retina exposure to beneficial chronobiological blue light.

In a non-limitative example, the fluorescent material may be a fluorescent dye which absorbs harmful blue light, in the 380-455 nm range, and re-emits light by fluorescence in the 460-530 nm range.

Figure 2:
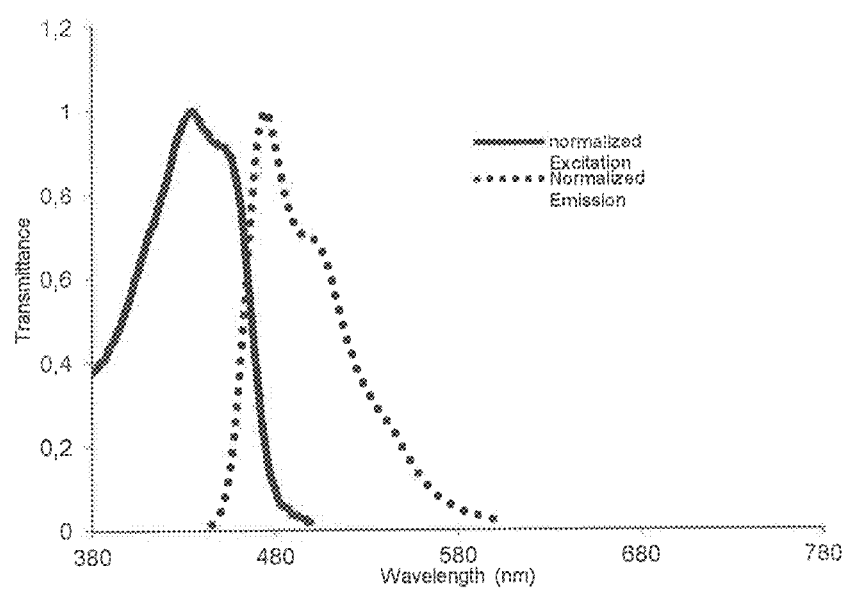
Figure 3:
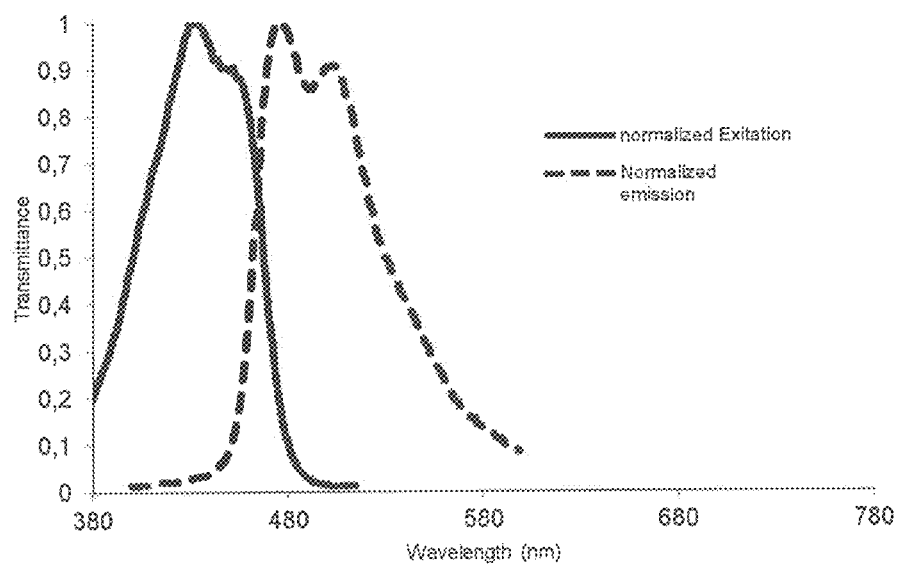

The fluorescent dye may be Cyan Fluorescent Proteins (CFP), inclusive enhanced-CFP (e-CFP) illustrated on FIGS. 2 and 3.

As illustrated on FIG. 2, Cyan Fluorescent Protein have a maximum wavelength of absorption of 435 nm and a maximum wavelength of emission of 475 nm.

As illustrated on FIG. 3, enhanced-CFP (e-CFP) have a maximum wavelength of absorption of 431 nm and a maximum wavelength of emission of 476 nm.

Advantageously, such fluorescent dye minimizes the amount of harmful blue light reaching the retina of the wearer while allowing retina exposure to beneficial chronobiological blue light.

With respect to fluorescents nanoparticules, they may include semiconductor nanoparticules, quantum dots, and core-shell particles. They may be chosen with limitation to these families from lead selenide (PbSe), Lead sulfide (PbS), Cadmium telluride (CdTe)/Cadmium sulfide (CdS), Cadmium selenide CdSe/Zinc sulfide ZnS or Cadmium selenide CdSe.

Advantageously, the fluorescents nanoparticules have a maximum wavelength of emission in the range 480 nm to 500 nm and an average particule size between 1, 9 and 6 nanometers The methods for incorporating one or several luminescent agents into the optical substrate or a functional coating are well known in the art.

In one embodiment, one or several luminescent agents may be incorporated into the optical substrate by being dispersed in a thermoplastic or thermoset polymer material during the manufacture of the substrate itself, for example by casting or injection molding, and/or in an adhesive material more particularly when a coating will be applied to the optical substrate by a lamination process, wherein the coating is supported by a flat thermoplastic film. The adhesive used to obtain cohesive adhesion between said film and said optical substrate may advantageously comprised such luminescent agents.

The luminescent agents can be incorporated into the optical substrate by methods well known in the art, for example impregnation or imbibition methods consisting in dipping the substrate in an organic solvent and/or water based hot coloration bath, preferably a water based solution, for several minutes.

In another embodiment, the luminescent agent is incorporated into at least one layer coated on the optical substrate.

Several luminescent agents can be incorporated in the substrate and/or the same or different layers deposited at the surface of the substrate.

In a preferred embodiment, the luminescent agent is incorporated in a layer deposited on the rear face of the optical substrate.

The luminescent agent may be incorporated into any functional coating and, for example, into a primer coating, a hard coating, an abrasion/scratch resistant coating e.g. varnish, an antireflection coating, an antistatic coating.

In some exemplary embodiments, the varnish may be a varnish comprises an organic solvent medium comprising at least one organic solvent or a mixture of organic solvents, e.g. sol-gel varnishes, acrylic varnishes or polyurethane varnishes.

The luminescent agent may be deposited when the layer is prepared from a liquid coating composition or may also be included in a coating in a separate process or sub-process by spin coating, dip coating or spray coating.

The luminescent agent can also be incorporated into a film that will be subsequently transferred, laminated, fused or glued to the optical substrate or the functional coating.

Those of skill in the art should appreciate that the desired amount of luminescent agent will vary depending on several factors including the nature and amount of the agent which is used. To this end, the optimal amounts of each compound can be determined by simple laboratory experiments.

According to an embodiment of the invention illustrated on FIG. 4, the optical system may further comprise a light emitting source 12, an optical waveguide 14 and a controller device 16.

The optical system according to the invention may be a non-immersive head mounted device, i.e. see through or see around head mounted display device.

The head mounted display device 10 according to the invention is advantageously housed in the form of eye-glasses. The housing has a spectacle frame defining the shape of the eye-glasses. Preferably, the head mounted display device 10 further comprises at least an optical lens 11 mounted in the spectacle frame and designed to be placed in front of a corresponding eye 18 of the wearer.

In one embodiment, the light emitting source may comprise one or several colored light-emitting diodes (LED), for example and preferably a blue-green LED having a central emission wavelength comprised between 460 nm to 530 nm.

The optical waveguide 14 is adapted to collect light emitted from the light emitting source 12 and to guide the collected light to the eye 18 of a wearer when the head mounted display device 10 is being worn by the wearer.

The optical waveguide 14, adapted to collect light emitted and to guide it to the eye 18 of the wearer, can comprise refractive optics, diffractive optics, Fourier optics and/or multiplexed beam splitters.

Refractive optics can be for example mirrors, prism combiner, semi-reflective dioptre and/or light-guide optical element (LOE).

Diffractive optics can be for example embedded grating and/or holographic optical elements.

The controller device 16 is adapted to control the emitted spectrum and/or radiance and/or light level emitted by the light emitting source 12.

Furthermore, the controller device 16 can be configured so as to provide gradient irradiances and/or spatially modulated irradiances. Thus, the exposure of the retina of the eye can be homogeneous and/or controlled allowing advantageously a better efficacy of a light treatment.

Advantageously, the head mounted display device according to the invention allows a simultaneous control of light properties: spatial distribution, directivity, intensity and spectrum of the light reaching the retina of the eye of the wearer.

Preferably, the illumination of the eye is peripheral in order to reduce the perception of the light treatment. Thus, the incidence angles of the light emitted by the light emitting source 12 and from the optical waveguide 14 are defined taking advantage of the Stiles-Crawford effect with peripheral incidence angles and of the cone density and distribution within the retina.

Controlling the direction and the diffusing angle of the light entering the pupil of the eye and reaching the retina provides a better focus of the light and a better intensity control of the light reaching the eye.

Advantageously, the light emitting source 12 and the controller device 16 are housed in the spectacle frame and in particular, in a sidepiece of the spectacle frame.

Preferably, the optical waveguide 14 can be embedded in or mounted in front of the optical lens 11.

Furthermore, the head mounted display device 10 comprises preferably at least one optical sensor 20 arranged to measure data relating to an incident light on the head mounted device 10 such as the ambient light.

The optical sensor 20 is adapted to measure the light level and/or spectrum of the ambient light.

The optical sensor 20 can be arranged in front of and/or behind the optical lens.

The optical sensor 20 may be positioned outwardly to see the real scene without alteration by the optical lens 11. Nonetheless, it may be disposed directly on the front face of the optical lens 11 as well as accommodated in the optical lens.

The controller device 16 is configured so as to control the light emitting source 12 based at least on the measured light level and/or spectrum data of the incident/ambient light.

More particularly, the optical sensor 20 may be:
  a micro-spectrometer
  a photodiode array, each photodiode with a specific bandwidth allowing the detection of particular light frequency
  a camera for complete real scene analysis or special object detection, like high luminance object
  more specialized sensor(s), for example for accurately detecting a light level, intensity and/or a wavelength to be eliminated.

The optical sensor 20 is in communication with the controller device 16 with a wired or wireless connection. This connection may further involve a sensor interface detailed below.

Advantageously, the controller device 16 is also configured so as to control the light emitting source 12 based on the day time and/or on the geo-localization of the head mounted display device 10. To this end, the head mounted display device 10 further comprises a real time clock 22 and/or a global positioning system (GPS) 24. The head mounted display device 10 can also comprise a sensor adapted for controlling the wearing time of the head mounted display device.

Indeed, the controller device 16 can control the start and/or the end of the light therapy or the retinal exposure duration of the light therapy.

The controller device 16 may comprise processing means 41. These latter components are not detailed, but may be any of common components used to design electronic systems, such as for example STM32 or Kinetis microcontroller or iMX6 processor. The controller device 16 may also comprise interfacing means. For instance, the sensor interface may allow the controller device 16 to functionally interface the optical sensor 20.

The interfacing means are not detailed, but may be any of common interfaces used to design electronic systems, such as for example $I^2C$ bus, Mipi interface, or any wired or wireless communication between components.

The controller device 16 may further comprise data storing means, for instance for storing measured and/or collected data. These latter are not detailed, but may be any of common non-transitory storage medium used to design electronic systems, such as for example SRAM memory, Flash memory, etc.

The controller device 16 may further comprise supplementary sensors or be communicatively connected to such supplementary sensors with these latters being or not comprised in some external devices. The supplementary sensors are not detailed, but may be any kind of touch sensors, pressure sensors, light sensors, temperature sensors, chronometers, displacement sensors, accelerometers, gyroscopes, magnetometers, or actimetry sensors. Thus, in particular embodiments, a displacement sensor may be used to automatically detect an activity (walking, running, standing or sitting). Other sensors (temperature, blood pressure, etc.) may also be used.

Wireless connection of the controller device 16 to an external processor is also possible; thus the management of the head mounted device 10 may be made by the use of the external processor and the control unit 16 advantageously needs less processing resources. The decision and way to activate the head mounted device 10 may be determined locally (on or near the head mounted device 10) or remotely (on the external device).

Said external devices or external processors may comprise a mobile phone, a smartphone, a control pad, an iPad, tablet, or a graphics pad. These devices or processors may get supplementary information about the environment of the device 10 and, if appropriate, the wearer (activity, health test, agenda, etc.), in order for the controller device 16 to take into account at least one of these supplementary information or measured data in controlling the light emitting source 12.

Wireless connection of the controller device 16 to the Internet is also possible, for instance via the external devices. In such a case, regulation may be done with information about the wearer and his environment coming from the Internet, and the management of the head mounted device may be performed by a remote controller comprised in an Internet server.

According to an embodiment of the invention, the head mounted display device 10 may further comprise an eye tracking device 28 adapted to detect position and/or movement of the eye 18 of the wearer. In the case of this preferred embodiment, the controller device 16 is configured so as to control the light emitting source 12 based at least on the detected position and/or movement of the eye of the wearer. The eye tracking device 28 can be arranged in front of and/or behind the optical lens 11.

Moreover, the controller device 16 can also be configured so as to personalize or control the light emitting source 12 based on a wearer profile defined by wearer parameters.

Such wearer parameters are related to the age of the wearer and/or the biological clock of the wearer and/or the activity of the wearer (working activity, sport activity, etc. . . . ) and/or ocular disease of the wearer and/or the type of physiological disorder of the wearer.

Such wearer data can be stored in the data storing means on a memory 26.

In one embodiment, such a memory 26 may be integrated in the head mounted display device 10 and housed in the frame.

Thus, such a head mounted device 10 allows a personalized management of the emitted light by the light emitting source 12 according to the wearer profile.

Furthermore, the controller device 16 can be configured so as to provide chronobiology regulation and/or affective disorders regulation and/or myopia reduction and/or prevention and/or epilepsy palliative treatment by controlling the light emitting source 12 to provide emission in the selected range of wavelengths between 460 nm and 530 nm with specific spatial and temporal patterns.

In operation, light from the light emitting source 12, preferably having a wavelength ranging from 460 nm to 530 nm, is launched into one end of the optical waveguide 14. The light emitting source 12 is controlled by the controller device 16 for modulating the emitted spectrum, the light intensity, the exposure time and duration preferably according to wearer parameters stored in the memory and according to date and time.

Moreover, the light emitting source 12 can be activated for example if the incident light received during the day and measured by at least the optical sensor 20 is less than a threshold predetermined according to wearer parameters.

The head mounted display device according to the invention results in an increase of the retinal exposure to the selected range of wavelengths within the blue-green range. The selected range of wavelengths is the best synchronizer of human non-visual biological functions.

The inventors have evidenced in a clinical study led in 2013 on 52 young healthy subjects that showed 2-weeks of continuously wearing optical filters that cut off more than 99% of wavelengths comprised between 460 nm and 520 nm is sufficient to induce a 1 hour shift in L5 (five least active hours) and M10 (10 most active hours) sleep-wake criteria.

By optimizing retinal light reception in between 460 nm and 500 nm, we induce the direct stimulation of ipRGC by melanopsin photoreception peaking at 480 nm for humans.

By taking into account the poor spatial density of ipRGC (only 1 to 3% of retinal ganglion cells) compared to that of rod photoreceptors, the probability of absorbing a photon is more than 1 million times lower of a given area of photostimulation. Thus, even if ipRGC phototransduction cascade is highly amplified, the inventors suspect that ipRGCs receive additional input from a complementary photoreception process involving rods. We have observed that ipRGCs may be responsive to lower levels of illumination than initially planned, confirming the role of rods. By extending the transmitted spectral range to 460-530 nm, we induce both the direct stimulation of ipRGC and the indirect stimulation by the incoming rod driven signals peaking near 500 nm.

In particular, this specific illumination range is the most potent stimulus for entraining endogenous rhythms to the daily light cycle with the two photoreceptive processes involved: the melanopsin-driven phototransduction mechanism within the ipRGC itself, peaking near 480 nm and indirect photoreception in rods, peaking near 500 nm.

Therefore, optical systems according to embodiments of the invention may be used in therapy and/or disease prevention.

Such device according to the invention may be used in therapy for treatment of subjects suffering from chronobiological disorders such as circadian rhythm sleep disorders, sleep disorders, pupil dilation, jet lag, delayed and advanced sleep phase syndromes, mood disorders, seasonal affective disorder such as depression or fatigue, postpartum depression, cancer risks, hormonal disorders, alertness disorders and cognitive performances, appetite and obesity, memory disorders, psychomotor disorders, body temperature deregulation, premenstrual disorders, epilepsy crisis and myopia. The device can help shift workers to adjust their biological clock to a new shift.

Indeed, the device according to the invention can compensate inadequate lighting conditions (lack of beneficial blue at specific moments) to help the biological clock to remain synchronized through the good blue/melatonin secretion relationship.

The present invention provides also a method to treat circadian rhythm sleep disorders comprising selectively allowing retinal exposure of an eye to at least one selected range of wavelengths of light in the visible spectrum of 460 nm to 530 nm, preferably of 480 nm to 520 nm.

In an embodiment, as already discussed, such device according to the invention may be used in myopia prevention and/or reduction. An adapted light therapy may contribute to reduce the risk of myopia onset by acting positively on the production cycle of dopamine. Dopamine is a retinal neurotransmitter associated with light adaptation. Dopamine has an impact on the eye length and thus on myopia. Recent research shows that dopaminergic cells are linked to intrinsically photosensitive retinal ganglion cells and that they are regulated by the chronobiological blue light at around 480 nm. This specific light may activate endogenous dopamine production, while a lack of this light (spectrum and/or light level) may inhibit dopamine production. The inhibition may in the long term contribute to the elongation of the eye.

It should be noted that the optical filter may be configured as a passive system or an active system. By passive system it is understood that the optical filter presents a filtering function which cannot be modified or changed. By active system, it is understood that the optical filter present at least a function that can be modified or changed by an external stimulation such as energy, actinic radiation, heating, etc. so that transmission of the selected range of wavelength of light may be switched on or off, or the light transmittance factor varied according to the time of day or the activity of the wearer or the exposure to light.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. An optical system having a spectral transmission profile having an average transmittance Ta between 380 nm and 780 nm and an average red light transmittance Tr between a first limit L1 and a second limit L2, with Tr<2*Ta/3 and L1=600 nm and L2=780 nm, and the optical system being configured to allow selectively retinal exposure of an eye to at least one selected range of wavelengths of light in the visible spectrum of 460 nm to 530 nm, wherein the optical system further comprises at least a luminescent agent which emits light within the at least one selected range of wavelengths of light; wherein the luminescence agent is a fluorescent material which emits light by fluorescence in the at least one selected range of wavelengths; and wherein the fluorescent material comprises fluorescent nanoparticles, wherein the fluorescent nanoparticles are quantum dots.

2. The optical system according to claim 1, wherein the optical system is configured to selectively emit light in at least the selected range of wavelengths of light in the visible spectrum.

3. The optical system according to claim 2, wherein L2=650 nm.

4. The optical system according to claim 3, wherein Tr<Ta/5.

5. The optical system according to claim 1, wherein the spectral transmission profile has an average blue light transmittance Tb between a third limit L3 and a fourth limit L4, with Tb<2Ta/3, for example Tb<Ta/5, with L3=380 nm and L4=455 nm.

6. The optical system according to claim 1, further configured to solar protection.

7. The optical system according to claim 1, wherein the at least one selected range of wavelengths of light is centered on a wavelength within the range of 480 nm to 510 nm, with a bandwidth in a range from 20 nm to 70 nm.

8. The optical system according to claim 1, wherein the fluorescent material is a fluorescent molecule which:
absorbs energy between 380 nm and 455 nm of the light spectrum and/or in the UV portion of the light spectrum; and
re-emits it in the selected range of wavelengths of light.

9. The optical system according to claim 8, wherein the optical system comprises an interferential filter.

10. The optical system according to claim 1, wherein the optical system is configured to selectively and substantially reflect light arriving on the front face of the optical system between L1 and L2 and/or L3 and L4.

11. The optical system according to claim 10, wherein the controller device is configured to provide chronobiology regulation or synchronisation and/or affective disorders regulation and/or myopia prevention and/or reduction and/or epilepsy palliative treatment by controlling the light emitting source to provide emission between 460 nm and 530 nm with specific spatial and temporal patterns.

12. The optical system according to claim 1, wherein the optical system further comprises:
a light emitting source;
an optical waveguide adapted to collect light emitted from the light emitting source and to guide the collected light to the eye of a wearer when the optical system is being worn by the wearer; and
a controller device adapted to control the emitted spectrum and/or radiance and/or light level emitted by the light emitting source so as to selectively emit light in the selected range of wavelengths.

13. The optical system according to claim 12, further comprising an optical sensor adapted to detect the light level and/or spectrum of the ambient light, and wherein the controller device is configured so as to control the light emitting source based at least on the detected light level and/or radiance and/or spectrum of the ambient light.

* * * * *